US007968531B2

(12) United States Patent
Cuevas Sanchez et al.

(10) Patent No.: US 7,968,531 B2
(45) Date of Patent: Jun. 28, 2011

(54) USE OF 2,5-DIHYDROXYBENZENESULPHONIC ACID IN THE PRODUCTION OF MEDICAMENTS FOR THE TREATMENT OF ANGIODEPENDENT DISEASES SUCH AS CANCER AND PSORIASIS

(75) Inventors: Pedro Cuevas Sanchez, Madrid (ES); Antonio Romero Garrido, Madrid (ES); Guillermo Gimenez Gallego, Madrid (ES); Serafin Valverde Lopez, Madrid (ES); Rosa María Lozano Puerto, Madrid (ES)

(73) Assignee: Action Medicines, S.L. (ES)

( * ) Notice: Subject to any disclaimer, the term of this patent is extended or adjusted under 35 U.S.C. 154(b) by 179 days.

(21) Appl. No.: 10/588,166

(22) PCT Filed: Feb. 16, 2005

(86) PCT No.: PCT/ES2005/070017
§ 371 (c)(1),
(2), (4) Date: Aug. 7, 2008

(87) PCT Pub. No.: WO2005/077352
PCT Pub. Date: Aug. 25, 2005

(65) Prior Publication Data
US 2008/0293816 A1    Nov. 27, 2008

(30) Foreign Application Priority Data
Feb. 17, 2004   (ES) .................................. 200400371

(51) Int. Cl.
*A61K 31/185*   (2006.01)
*A61K 31/56*    (2006.01)
*A01N 37/00*    (2006.01)
*A01N 45/00*    (2006.01)

(52) U.S. Cl. ........................ 514/171; 514/553; 514/576
(58) Field of Classification Search ........................ None
See application file for complete search history.

(56) References Cited

U.S. PATENT DOCUMENTS

| 3,954,767 | A | * | 5/1976 | Esteve-Subirana ........... 544/403 |
| 4,115,648 | A | | 9/1978 | Esteve-Subirana |
| 4,837,378 | A | | 6/1989 | Borgman |
| 4,970,202 | A | | 11/1990 | Trigger |
| 5,519,018 | A | | 5/1996 | Matusch et al. |
| 5,698,595 | A | | 12/1997 | Boelle et al. |
| 6,281,203 | B1 | | 8/2001 | Touzan et al. |
| 6,664,406 | B1 | | 12/2003 | Coupland et al. |
| 6,787,573 | B2 | | 9/2004 | Nottet |
| 2002/0143052 | A1 | | 10/2002 | Lan-Hargest et al. |
| 2003/0216418 | A1 | | 11/2003 | Stogniew et al. |
| 2004/0167222 | A1 | | 8/2004 | Brooks et al. |
| 2005/0175559 | A1 | | 8/2005 | Dinardo et al. |
| 2006/0258730 | A1 | | 11/2006 | Allegretti et al. |
| 2007/0032471 | A1 | | 2/2007 | Torrens-Jover et al. |
| 2007/0149618 | A1 | | 6/2007 | Cuevas Sanchez et al. |
| 2008/0113947 | A1 | | 5/2008 | Cuevas Sanchez et al. |
| 2008/0113948 | A1 | | 5/2008 | Cuevas Sanchez et al. |
| 2008/0114060 | A1 | | 5/2008 | Cuevas Sanchez et al. |
| 2008/0114063 | A1 | | 5/2008 | Cuevas Sanchez et al. |
| 2008/0114075 | A1 | | 5/2008 | Cuevas Sanchez et al. |
| 2008/0125485 | A1 | | 5/2008 | Cuevas Sanchez et al. |
| 2008/0125486 | A1 | | 5/2008 | Cuevas Sanchez et al. |
| 2009/0111779 | A1 | | 4/2009 | Cuevas Sanchez et al. |

FOREIGN PATENT DOCUMENTS

| EP | 0 204 987 B1 | 11/1991 |
| EP | 1 719 509 A1 | 11/2005 |
| WO | WO 96/17589 | 6/1996 |
| WO | WO 96/25159 | 8/1996 |
| WO | WO 2005/013962 | 2/2005 |
| WO | WO 2005/077352 | 8/2005 |
| WO | WO 2006/029484 | 3/2006 |
| WO | WO 2006/069806 | 7/2006 |

OTHER PUBLICATIONS

Goodman et al. [Editors] "Chapter 198: Principles of Cancer Therapy." Cecil's Textbook of Medicine (Twenty-First Edition, vol. 1). W.B. Saunders Company, 2000. pp. 1060-1074.*
Actinic Keratosis and Other Precancers. The Skin Cancer Foundation. www.skincancer.org, 2008.
Arhanic, V., et al., "Attempts at Treating Rubeosis with Angioprotective Agents" Annals of the Dr. M. Stojanovic Hospital (1976) vol. 15, No. 2 pp. 120-123 (with English translation).
Banker et al. Modern Pharmaceutics, 3ed.; Marcel Dekker, New York, 1996, p. 596.
Barrett's disease: http://digestive-system.emedtv.com/barrett's-esophagus/casues-of-Barrett's-esophagus.html, Nov. 2006.

(Continued)

*Primary Examiner* — Brandon J Fetterolf
*Assistant Examiner* — Anna Pagonakis
(74) *Attorney, Agent, or Firm* — Frommer Lawrence & Haug LLP

(57) ABSTRACT

The invention relates to the use of 2,5-dihydroxybenzenesulfonic acid in the production of medicaments for the treatment of angiodependent diseases. More specifically, the invention relates to the use of the aforesaid compound and, in particular, the calcium and potassium salts thereof, for the treatment of two angiodependent diseases, which present a reduction in the apoptosis, namely cancer and psoriasis. The invention also discloses the antiproliferative, antimigratory, antiangiogenic and proapoptotic capacity of said family of compounds in non-quiescent cells. In addition, the invention details the potentiating effect of said compounds on known cytostatic medicines in the treatment of tumours and, specifically, on gliomas. The invention further relates to the therapeutic efficacy of said compounds, based on the combined antiproliferative, antiangiogenic and proapoptotic capacities thereof, in the treatment of chronic psoriatic plaques.

6 Claims, 9 Drawing Sheets

OTHER PUBLICATIONS

Figure 1:
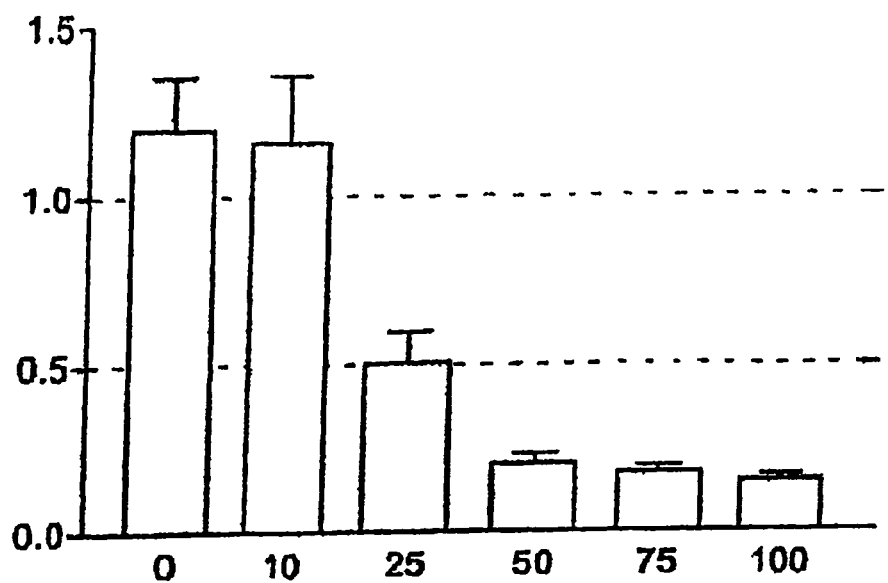
Figure 1:
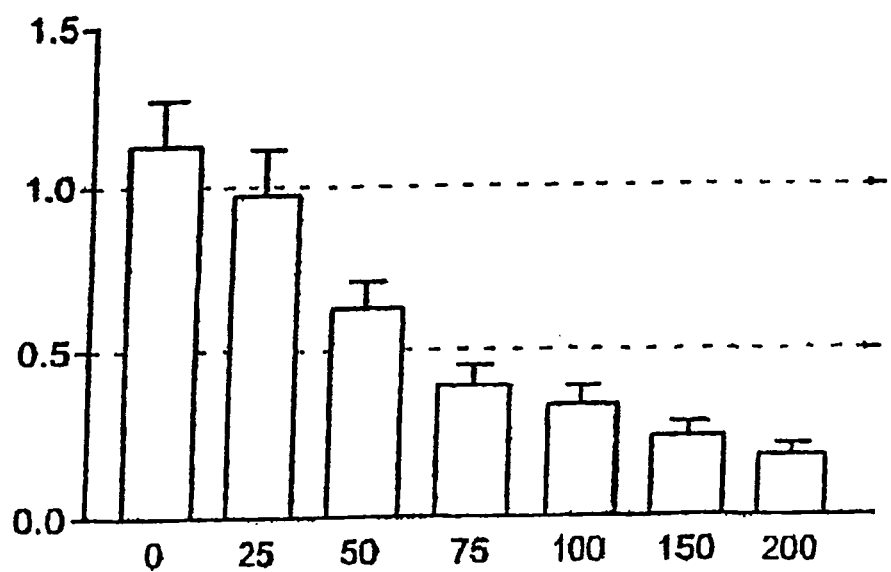

Brannon, http://dermatology.about.com/es/eczemadermatitis/a/atopictx.htm. Atopic Dermatitis Treatment.

Catalogo de especialidades farmaceuticas 1991, Consejo General de Colegios Oficiales De Farmaceuticos, Madrid, Spain, p. 674 Acnisdin and Acnisdin Retinoico entries (with summary in English).

Crohn's disease: http://cholitis.emedtv.com/crohn'sdisease/crohn's-disease-causes.html; (2008).

Cuevas et al. Dobesilate in the treatment of plaque psoriasis. Eur. J. Med. Res, 10, 373-376 (2005).

Cuevas, P. et al., Treatment of Basal Cell Carcinoma with Dobesilate, Journal of the American Academy of Dermatology, vol. 53, No. 3 (2005), pp. 526-527.

Definition of rosacea from American Heritage Medical Dictionary, 2007, www.freedictionary.com.

Divers et al. Curtis., 2004, vol. 73, No. 4, pp. 257-262 (Abstract attached).

Dormond O and Rüegg C, Inhibition of tumor angiogenesis by non-steroidal anti-inflammatory drugs: emerging mechanisms and therapeutic perspectives, Drug Resistance Updates (2002) 4, 314-321.

Gambichler T, et al., Cytokine mRNA expression in basal cell carcinoma, Arch Dermatol Res (2006) 298: 139-141.

Goldman et al. [editors] "Principles of Cancer Therapy." Cecil's Textbook of Medicine (Twenty-First Edition, vol. 1). W.B. Saunders Company. 2000, pp. 1060-1074.

Graber, R., et al., Calcium Dobesilate protects human peripheral blood mononuclear cells from oxidation and apoptosis, Apoptosis, vol. 3, No. 1 (1998) pp. 41-49.

Hodge D, et al., The role of IL-6 and STAT3 in inflammation and cancer, European Journal of Cancer 41 (2005) 2502-2512.

Hornheide et al. British Journal of Dermatology, 2005, vol. 152, pp. 939-947.

Hornick, JL, et al. "A New Chemically Modified Chimeric TNT-3 Monoclonal Antibody Directed Against DNA for the Radioimmunotherapy of Solid Tumors" Cancer Biotherapy & Radiopharmaceuticals (1998) vol. 13, No. 4, pp. 255-268.

Jee S-H, et al., Interleukin-6 Induced Basic Fibroblast Growth Factor-Dependent Angiogenesis in Basal Cell Carcinoma Cell Line via JAK/STAT3 and PI3-Kinase/Akt Pathways, J Invest Dermatol (2004)123:1169-1175.

Jee S-H, et al., "Overexpression of interleukin-6 in human basal cell carcinoma cell lines increases anti-apoptitic activity and tumorigenic potency", Oncogene (2001) 20, 198-208.

Jee S-H, et al., "The Phosphotidyl Inositol 3-Kinase/Akt Signal Pathway is Invovled in Interleukin-6-mediated Mcl-1 Upregulation and Anti-apoptosis Activity in Basal Cell Carcinoma Cells", J Invest Dermatol (20020 119: 1121-1127.

Johnson et al. British J. of Cancer, 2001, 84(10): 1424-1431.

Jordan VC. Nature Reviews: Drug Discovery, 2, 2003, p. 205.

Kaur et al. An open trial of calcium dobesilate in patients with venous ulcers and stasis dermatitis. International Journal of Dermatology. 2003, 42, 147-152.

Khawli, LA, et al. "Comparison of Recombinant Derivatives of Chimeric TNT-3 Antibody for the Radioimaging of Solid Tumors" Hybridoma and Hybridomics (2003) vol. 22, No. 1 pp. 1-10.

Lameynardie, S. et al., Inhibition of choroidal angiogenesis by calcium dobesilate in normal Wistar and diabetic GK rats, Eur J of Pharm, vol. 510 (2005) pp. 149-156.

Lens et al. Br. J. Nurs., 2008, vol. 17, No. 5, pp. 300-305 (Abstract attached).

Losa, G., et al., Prevention of Oxidation and Apoptosis in Human Peripheral Blood Mononuclear Cells Exposed to Calcium Dobesilate, Int'l J of Angiology, vol. 8 (1999) pp. 511-515.

Newell B, et al., "Comparison of the microvasculature of basal cell carcinoma and actinic keratosis using intravital microscopy and immunohistochemistry" British Journal of Dermatology 2003: 149; 105-110.

Nour, A.F., et al., Preliminary Clinical Study with Calcium Dobesilate in Fibrocystic Disease of the Breast, a pilot study, Acta Therapeutica, vol. 12, No. 3 (1986) pp. 233-241.

O'Grady A, et al. "COX-2 Expression Correlates with Microvessel Density in Non-Melanoma Skin Cancer from Renal Tranplant Recipients and Immunocompetent Individuals", Hum Pathol (2004) 35: 1549-1555.

Oh C-K, et al., "Expression of Basic Fibroblast Growth Factor, Vascular Endothelial Growth Factor, and Thrombospondin-1 Related to Microvessel Density in Nonaggressive and Aggressive Basal Cell Carcinomas" Journal of Dermatology (2003) vol. 30: 306-313.

Remington's Pharmaceutical Sciences, pp. 420-425, 1980.

Ruiz, E. et al., Calcium Dobesilate Increases Endothelium- Dependent Relaxation in Endothelium-Injured Rabbit Aorta, Pharmacological Research, vol. 38, No. 5 (1998), pp. 361-366.

Rutkowski, Suzanne; Asthma Magazine, p. 9-12, Jul./Aug. 2001.

Sausville et al. (Cancer Research, 2006, vol. 66, pp. 3351-3354).

Schon et al. 2005, N. England J. Med. 352: 1899-912.

Sintov et al. Journal of Controlled Release, 2002, vol. 79, pp. 113-122.

Skov et al., "Basal cell carcinoma is associated with high TNF-χ polymorphism at position—308" Experimental Dermatology, 2003, 12, 772-776.

Staibano S et al., "The Prognostic Significance of Tumor angiogenesis in Nonaggressive and Aggressive Basal Cell Carcinoma of the Human Skin" Hum Pathol 1996, 27, 695-700.

Stanton A, et al. "Expansion of Microvascular Best and Increased Solute Flux in Human Basal Cell Carcinoma in Vivo, measured by Fluorescein Video Angiography" Cancer Research (2003) 63: 3969-3979.

Stanwell, C., et al., The Erbstatin Analogue Methyl 2,5-Dihydroxycinnamate Cross-Links Proteins and is Cytotoxic to Normal and Neoplastic Epithelial Cells by a Mechanism Independent of Tyrosine Kinase Inhibition, American Association for Cancer Research, Baltimore, MD, vol. 55, No. 21 (1995) pp. 4950-4956.

Stockfleth et al. Successful treatment of actinic keratosis with imiquimod cream 5%: a report of six cases. British Journal of Dermatology, 2001; 144: 1050-1053.

Takatsuka et al. Various Analogues to Anthranilic Acid and their Anti-Cancer effects. Mie Medical Journal. vol. XVII, No. 1, 1997.

Tjiu J-W, et al., "Cyclooxygenase-2 Overexpressionin Human Basal Cell Carcinoma Cell Line Increases Antiapoptisis, Angiogenesis, and Tumorigenesis" Journal of Investigative Dermatology (2006) 126: 1143-1151.

Tjiu J-W, et al., "Tuor-Associated Macrophase-Induced Invasion and Angiogenesis of Human Basal Cell Carcinoma Cells by cyclooxygenase-2 Induction" Journal of Investigative Dermatology (2009) 129: 1016-1025.

Vippagunta et al., Advanced Drug Delivery Reviews, 48, 2001 pp. 3-26.

Wolff et al. Burger's Medicinal Chemistry and drug discovery, Fifth Edition. vol. 1: Principles and Practices. 1995.

Yamada, K., et al., Inhibitory Effect of Diacetyl Gentisic Acid on Melanogenesis, Journal of Japanese Cosmetic Science Society, Nihon Koshohin Kagakkai, Tokyo, JP, vol. 22, No. 3 (1998) pp. 169-174.

Zaragoza D. F. Side reactions in organic synthesis a guide to successful synthesis design, Weinheim: Wiley-VCH, Vertag Gmbh & Co., KGaA, 2005, Preface.

International Search Report for WO05077352 mailed Jun. 22, 2005.

International Search Report for WO2008020040 mailed Feb. 19, 2008.

International Search Report for WO2008020039 mailed Jul. 15, 2008.

International Search Report for WO2008020030 mailed Nov. 9, 2007.

International Search Report for WO2008020028 mailed Nov. 14, 2007.

International Search Report for WO2008020027 mailed Feb. 22, 2008.

International Search Report for WO2008020042 dated Dec. 6, 2007.

International Search Report for WO2008020034 mailed Dec. 3, 2007.

International Search Report for WO2008020033 mailed Nov. 30, 2007.

International Search Report for WO2008020032 mailed Nov. 26, 2007.
International Search Report for WO2008020031 mailed Nov. 28, 2007.
International Search Report for WO2008020037 mailed Nov. 30, 2007.
International Search Report for WO2008020026 mailed Nov. 28, 2007.
International Search Report for WO2008020025 mailed Nov. 27, 2007.
PCT International Search Report mailed on Jun. 22, 2005 in corresponding International Application No. PCT/ES2005/070017.
Written Opinion of the International Searching Authority mailed on Jun. 22, 2005 in corresponding International Application No. PCT/ES2005/070017.
PCT International Search Report mailed on Nov. 27, 2007 in corresponding International Application No. PCT/EP2007/058438.
Written Opinion of the International Searching Authority mailed on Nov. 27, 2007 in corresponding International Application No. PCT/EP2007/058438.
Reply to the Written Opinion in corresponding International Application No. PCT/EP2007/058438.
PCT International Search Report mailed on Feb. 22, 2008 in International Application No. PCT/EP2007/058440.
Written Opinion of the International Searching Authority mailed on Feb. 22, 2008 in International Application No. PCT/EP2007/058440.
Reply to the Written Opinion in International Application No. PCT/EP2007/058440.
English Translation of Acnisdin and Acnisdin Retinoico entries in Catalogo de especialidades farmaceuticas 1991, Consejo General de Colegios Oficiales De Farmaceuticos, Madrid, Spain, p. 674.
Travis L et al. Drugs of Today 38:847-865 (2002).
Jegasothy BV Arch Dermatol 128:781-785 (1992).
Banarroch IS et al Ophthalmic Res 17:131-138 (1985).
Lozano RM J Mol Biol 281:899-9115 (1998).
Trozak. Cutis. Chatham 64:315-318 (1999).
Wollina V et al. Clin Rheumatol 20:406-410 (2001).
Niwa Y et al. B J Dermatol 149:960-967 (2003).
Michal M et al. Thromb Res 51:593-605 (1988).
Benakis A et al. Therapie 29:211-219 (1974).
Suscheck C et al. Bt J Pharmacol 122:1502-1508 (1997).
Angulo J et al. Br J Pharmacol 139:854-862 (2003).
Brunet et al Fundam Clin Pharmacol 12:205-212 (1998).
Kocak M et al Int J Dermatol 42:789-793 (2003).
Karasek MA Cutis 64:319-322 (1999).

* cited by examiner

USE OF 2,5-DIHYDROXYBENZENESULPHONIC ACID IN THE PRODUCTION OF MEDICAMENTS FOR THE TREATMENT OF ANGIODEPENDENT DISEASES SUCH AS CANCER AND PSORIASIS

SCOPE OF THE INVENTION

This invention refers to a pharmaceutical composition that comprises the 2,5-dihydroxybenzenesulfonic acid, and its employment in the preparation of a medicine for treatment of diseases characterized by an intense cell proliferation, vascularization (angiodependent diseases) and more specifically angiodependent diseases also having reduction of the apoptosis, as it is the case for example in cancer or psoriasis.

BACKGROUND OF THE INVENTION

Malignant tumors are characterized, besides from the uncontrolled cellular proliferation, by their capacity to invade normal peritumoral tissues. Tumor invasion is a complex process developed according to the following consecutive stages: a) adhesion of the tumor cells to proteins of the extra-cellular matrix; b) degradation of the proteins of the extra-cellular matrix by proteases that create extra-cellular spaces that the tumor cells use to, c) migrate through a dynamic and complex mechanism that requires synthesis of new portions of the cytoplasmic membrane and reorganization of the cytoskeleton (Giese A, Westphal M. Neurosurgery 1996; 39: 235-252). The cells that from the tumor mass invade the normal peritumoral-tissue have their genetic program of cellular death disabled and therefore, the tumor cells that migrate to invade the peritumoral intact tissues, elude the apoptosis (Mariani I et al. Clin Cancer Res 7:2480-2489, 2001). When the grouped tumor cells reach 2 to 3 $mm^3$ volume, the tumor cells synthesize large amounts of angiogenic factors to counteract the hypoxic situation of this primary tumor, (Folkman J. N. Engl J Med 285: 1182-1186, 1971; Carmeliet P, Jain R K. Nature 407: 249-257, 2000; Yancopoulos G D et al. Nature 407: 242-248, 2000) that activate the peritumoral blood vessels so that they form new blood vessels (angiogenesis) that invade the tumor to supply the oxygen and the nutrients and eliminate products from the tumor catabolism. The same cellular processes that occur during the tumor invasion (motility and absence of apoptosis) occur centripetally during tumor angiogenesis. Therefore, the inhibition of the invasive capacity of the tumor cells and of the endothelial cells should produce a delay in tumor growth by inhibiting the tumor expansion, reducing angiogenesis and promoting apoptosis. Therefore, an effective treatment against cancer should inhibit the migration, the angiogenesis and increase apoptosis without producing these effects in normal cells.

There are numerous anti-tumor and antiangiogenic agents at various stages of clinical development in oncology (Brem S. Cancer Control 6: 436-458, 1999), of which a significant number are polypeptides that the body uses to counteract the effect of the positive regulators of angiogenesis (Hagerdom M, Bikfalvi A. Crit. Rev One Hemat 34: 89-110, 2000). However, when said polypeptides are compared with compounds with a significantly lower molecular weight, their pharmacological inconveniences become evident. On the other hand, it has been proven that different synthetic compounds containing aromatic rings in their molecular structure and acting as inhibitors of the mitogenic activity induced by growth factors are cytotoxic for quiescent or non tumor cells (Lozano R M J Mol Biol 281: 899-9115, 1998). Therefore, there is still need to find compounds with anti-tumor, antiangiogenic and proapoptotic activity with low toxicity for healthy, quiescent, non tumor cells. There is presently a great interest for the search of new therapeutic indications for old medicines. In this connection, it has been recently proven that different antibiotics, besides from their antimicrobial activity, have antiproliferative effects, such in the case of rapamycin (Morice M C et al. N Engl J Med 346: 1773-1780, 2002), or of the neomycin (Cuevas P. et al. Neurol Res 224: 389-391, 2002); or are useful as anxiolytics such as norfloxacin (fluoroquinolone) (Johnstone T B et al. Nat Med 10; 31-32, 2004).

Psoriasis is an angiodependent chronic disease that affects 2-3% of the world population and is characterized by epidermic hyperplasia, dermo-epidermic infiltration of inflammatory cells and T lymphocytes, and a very evident development of vascularization (Robert C, Kupper T. S. New Engl. J. Med, 1999; 341:1817-1828), together with a reduction of the cell death due to apoptosis (Kocak M et al. Int J Dermatol 42: 789-793, 2003). Presently, there is no curative treatment for psoriasis. The antipsoriatic treatment may be topical or systemic, depending on the extension and severity of the disease. The mostly used anti psoriatic topical therapy consists of different types of corticoids, but the extended use of these compounds is associated with skin atrophy, stretch marks and telangiectasia (Baker B S, Fry L. Cutis 1999; 64: 315-318). The systemic therapy with immunosuppressant medicines is associated to very severe side effects (Wolina V. et al. Clin Rheumatol 2001: 20: 406-410). For example, the use of cyclosporine for treatment of psoriasis may produce nephrotoxicity (interstitial fibrosis and tubular atrophy), hypertension, hypomagnesaemia, hypercalcemia and hepatic dysfunction (Travis L, Weinberg J M. Drugs of Today 2002; 38: 847-865). The standing use of another immunosuppressant medicine for treatment of psoriasis, tacrolimus, may produce hypertension, nephrotoxicity and immunosuppression (Jegasothy B V et al. Arch Dermatol 1992; 128: 781-785). It has been recently described that the topic application of the tacrolimus immunosuppressant accelerates carcinogenesis in mouse skin (Niwa Y, Terashima T, Sumi H. B J Dermatol 2003; 149: 960-967). Therefore, there is need for new antipsoriatic compounds proving to be efficient without producing evident side effects such as those associated with the most common anti-psoriatic treatments.

The 2,5-dihydroxybenzenesulfonic acid is a derivative of the 2,5-dihydroxybenzoic acid, pharmacologically prescribed in the form of different salts (mainly calcium, potassium, and magnesium), which provides stability. The 2,5-dihydroxybenzenesulfonic acid has been used since the 70's as an oral vasculotropic medicine (Berthet P et al Int J. Clin Pract 53: 631-636, 1999).

The 2,5-dihydroxybenzenesulfonic acid inhibits platelet aggregation, increase of capilar permeability and blood viscosity in patients with diabetic retinopathy (Bayer J. et al. Dtsch. Mod Wschr 1980; 46: 160-1608; Banarroch I. S. et al. Ophthalmic Res 1985; 17; 131-138; Michal M, Giessinger N. Thromb Res 1988; 51: 593-605). The metabolism and the pharmacokinetics of this compound in the human being is known since year 1974 (Benakis A. et al. Thérapie 1974; 29: 211-219). Recent experiments have proven that the 2,5-dihydroxybenzenesulfonic acid increases the activity of the endothelial isoform of the nitric oxide synthase [endothelial nitric oxyde synthase (eNOS)] in rat endothelial cells without producing cytotoxic effects (Suscheck C. et al. Bt J Pharmacol 1997; 122: 1502-1508). In addition, the 2,5-dihydroxybenzenesulfonic acid potentiates the in vitro relaxation of human penile arteries (Angulo J et al. Br J Pharmacol 2003; 139: 854-862). There is experimental evidence that the 2,5- dihydroxybenzenesulfonic acid (formulated as a calcium or magnesium salts) possesses in vitro antioxidant activities (Brunet J et al. Fundam Clin Pharmacol 12: 205-212, 1998).

The present invention is based on the discovery of new activities of the 2,5-dihydroxybenzenesulfonic acid and/or its salts, associated to their antiproliferative, anti migratory, anti-angiogenic and proapoptotic capacity in non quiescent cells, activities that combined, justify their employment as a useful compound for treatment of angiodependent diseases such as the case of cancer, characterized by hyperproliferation, cell invasion and excessive angiogenesis, together with a deficit in cell death due to apoptosis, without causing toxicity for non-tumor healthy or quiescent cells. Gliomic tumor cells have been used in experiments because gliomas are very invasive tumors with a significant angiogenic capacity and a significant apoptotic deficit (Merzak A, Pilkington G J. Cancer Metastasis Rev 16: 155-177, 1997).

The present invention is also based on the proven fact that the 2,5-dihydroxybenzenesulfonic acid and/or its salts possess, in a combined form, antipoliferative, antiangiogenic, and proapoptotic effects and therefore its therapeutic efficacy has been evaluated in chronic psoriatic plaques characterized by epidermic hyper-proliferation, acute dermal angiogenesis and apoptotic deficit (Karasek M A, Cutis 64: 319-322, 1999).

This invention relates then to the search of new treatments for cancer and other angiodependent diseases an it is based on the fact that the 2,5-dihydroxybenzene sulfonic acid and/or its salts have proven their capacity to inhibit growth and migration and induce the apoptosis in in vitro tumor cells as well as the capacity to inhibit the in vivo angiogenesis induced by fibroblast growth factor (FGF). Therefore, due to the combination of these abilities, the mentioned compounds become useful for the treatment of malignant tumors and hematological neoplastic diseases as well as for treatment of other severe vascularization related pathologies (angiodependent diseases).

DESCRIPTION OF THE INVENTION

The 2,5-dihydroxybenzenesulfonic acid formulated in the form of salt is a commercial product (for example, the potassium salt may be acquired at Merck Farma y Química SA, Mollet del Vallés, Barcelona) with the following molecular formula:

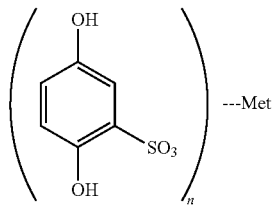

in which Met=Metal and n is a function of the metal valence used in the salt. Generally n 0 1 or 2 for being the metal cation former of the salt, univalent (K) or divalent (Ca ó Mg).

The new biological activities of the 2,5 dihydroxybenzenesulfonic acid do not depend of the cation bond to the benzene ring because the 2,5-dihydroxybenzenesulfonic acid formulated with any salt has similar effects in the inhibition of cell proliferation, migration and angiogenesis. This invention only describes the activities of the 2,5-dihydroxybenzenesulfonic acid formulated as potassium and calcium salt without forgetting that within the scope of this invention is any pharmaceutically acceptable salt of the compound. The term "pharmaceutically acceptable salts" include metal salts or addition salts which can be used in pharmaceutical forms. The pharmaceutically acceptable salts of the 2,5-dihydroxybenzenesulfonic acid can be obtained from organic or inorganic acids or bases, through conventional methods, by making the appropriate acid or base react with the compound.

The pharmaceutical compositions containing the 2,5-dihydroxybenzenesulfonic acid can be presented in any adequate administration form, for example, systemic, oral, parenteral, urethral, rectal or topical administration, for which the necessary pharmaceutically acceptable excipients will be included for formulation of the desired form of administration.

The following examples illustrate and support the invention and should not be considered as limitations of the scope of the invention.

Example 1

Figure 2:
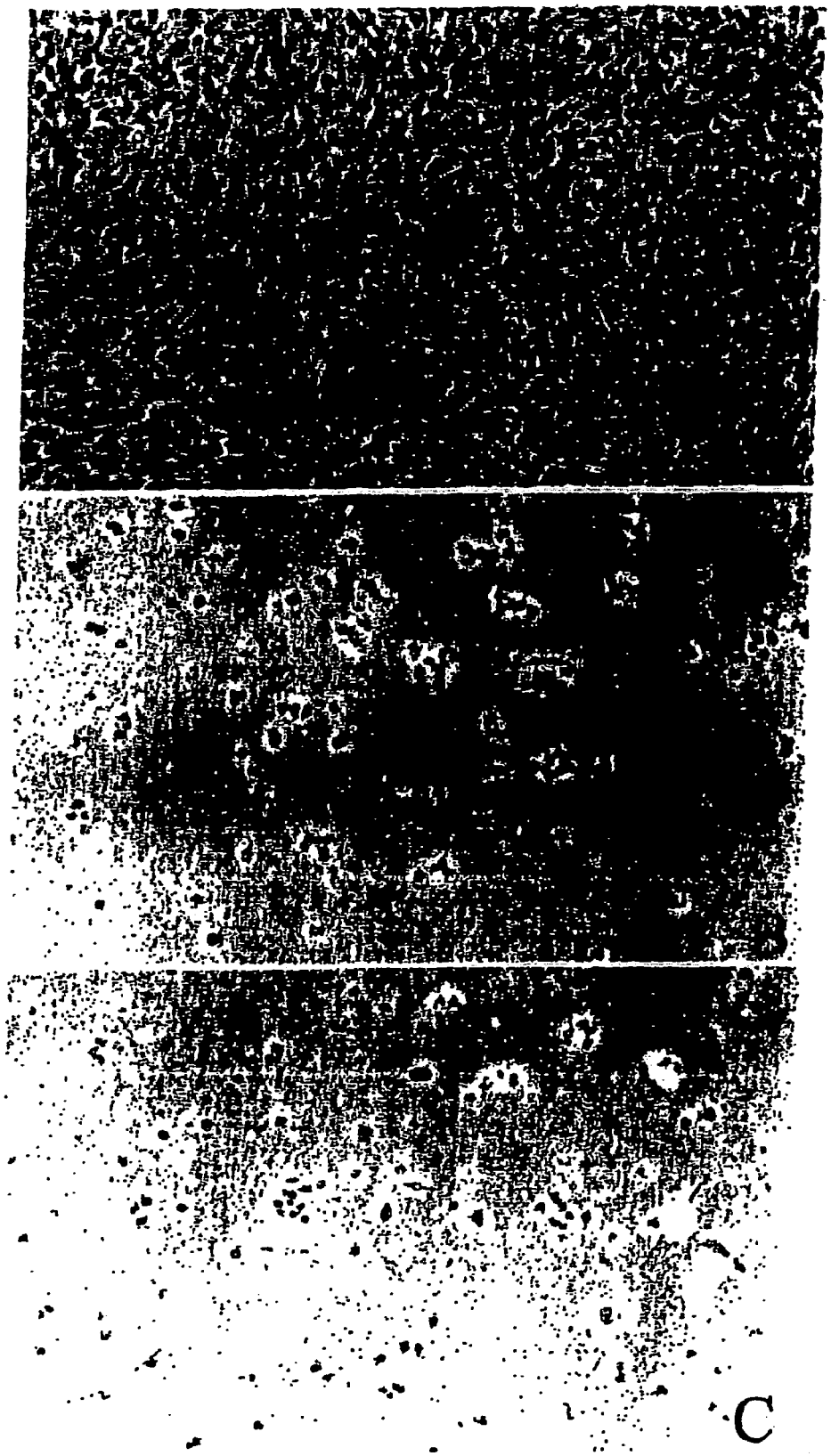

Illustrative Assay of the Anti-Proliferative Ability of the 2,5-Dihydroxybenzenesulfonic Acid This in vitro study was carried out in three different triplicate experiments with rat gliomic cells (C6 line). The cells were cultured in a medium formed by DMEM Dulbecco's modified Eagle's Medium (Gibco. Paisley UK), 7.5% of fetal serum (Gibco) 10 units/ml of penicillin (Gibco) and 10 µg/ml of streptomycin (Gibco). The cultures were kept in a humid atmosphere at 37° C. To evaluate the effect of the 2,5-dihydroxybenzenesulfonic acid on the cell proliferation, $2 \times 10^4$ C6 cells per well were seeded in 24-well (15 mm of diameter) plates. The experimental cultures were treated during 48 hours with different micro molar concentrations (µM) of the compound (calcium or potassium salt of the 2,5-dihydroxybenzenesulfonic acid). The control cultures lived 48 hours, without adding the compound. Photographs of the cultures were taken after 48 hours using an inverted microscope and then, the cultures were colored with crystal violet (Merck Farma y Química SA. Mollet del Vallés, Barcelona) and processed to determine the number of cells per well, using a spectrum photometric method. As shown in FIG. 1, treatment with different concentrations of the compound produces a dose-dependent inhibition of cell proliferation, obtaining 88% inhibition with a concentration of 100 µM of the calcium salt of the 2,5-dihydroxybenzenesulfonic acid (A). With the same concentration of the potassium salt of the 2,5-dihydroxybenzenesulfonic acid, a 74% inhibition (B) was obtained. The $IC_{50}$ is near to 25 µM for the calcium salt and between 40 and 50 µM for the potassium salt. Comparing FIG. 1A with FIG. 1B, it is observed that to obtain the same percentage of inhibition in cell proliferation after treatment with the calcium salt of the compound, a double concentration of potassium salt is necessary to obtain the same effect. This is due to the fact that the calcium salt of the compound contains two active principle moles (2,5-dihydroxybenzenesulfonic acid) that separate from salt in aqueous solution. FIG. 2 shows the image of the C6 cells culture after 48 hours without treatment (A), another image corresponding to the C6 cells culture treated for 48 hours with a concentration of 50 µM of the calcium salt of the 2,5-dihydroxybenzenesulfonic acid (B) and a third one corresponding to a culture of C6 cells treated during 48 hours with 100 µM of the potassium salt of the acid (C). This study shows that the treatment with the compound inhibits proliferation in neoplastic cells and corroborates the antiproliferative effect of the compound observed in normal vascular smooth muscular cells stimulated in vitro with mitogenic factors (Parés-Herbute N et al.

Int J Angiol 8: S5-S10, 1999). To distinguish if the antiproliferative activity of the 2,5-dihydroxybenzenesulfonic acid is mediated by a cytotoxic or a proapoptotic effect, we conducted different experiments detailed in the following example:

Example 2

Illustrative Assay of the Proapoptotic Ability of the 2,5 Dihydroxybenzenesulfonic Acid This assay was carried out with C6 cells cultured in vitro according to the procedure described in example 1. To demonstrate the proapoptotic effect of the analyzed compounds we have used two different methods that detect the intracellular fragmentation of the DNA and the apoptotic nuclei in situ.
Detection of the Intracellular Fragmentation of the DNA.

The enzymatic immunoassay methods to quantify the DNA fragments associated to histones may be considered suitable to determine the onset of apoptosis (Aragane Y et al. J Cell Biol 1998; 140: 171-182). This method allows to differentiate death due to necrosis from death due to apoptosis since in necrosis the cytoplasmic membrane is fragmented and the DNA appears in the culture medium, while in apoptosis, the fragmented DNA remains in the interior of the cell because the plasma membrane remains intact (Aragane Y et al. J Cell Biol 140: 171-182, 1998).

Figure 3:
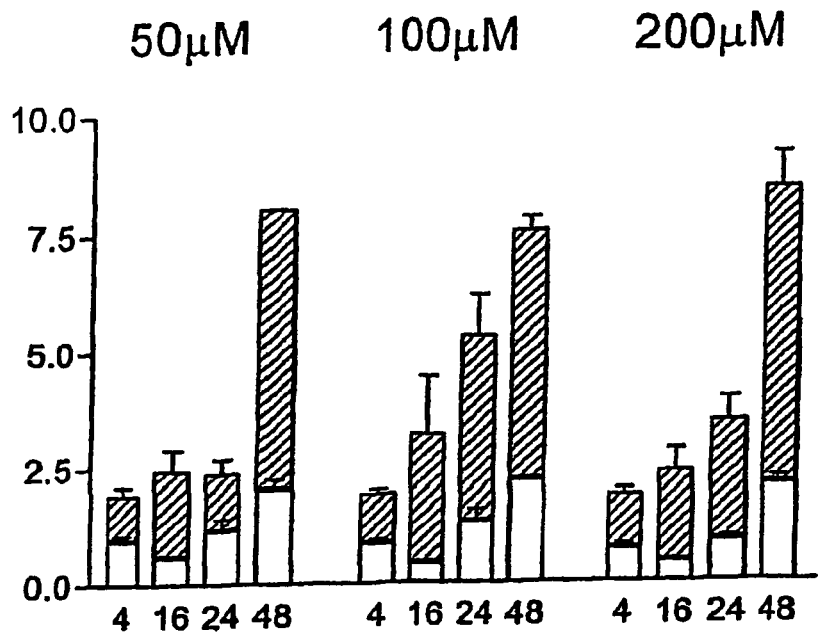
Figure 3:
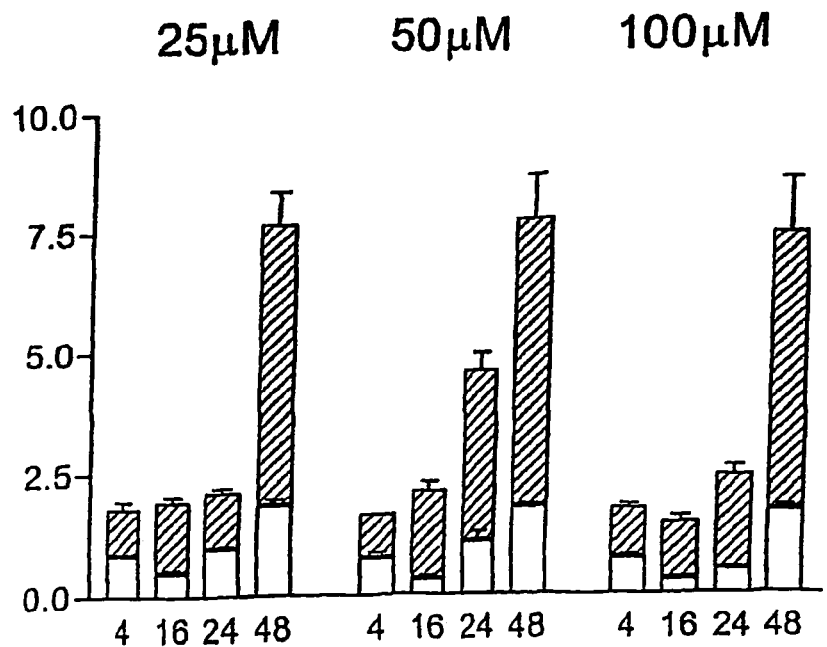

Using the Cell Death Detection ELISA$^{plus}$ kit (Boehringer Mannheim, Mannheim, Germany) in accordance with the manufacturer's instructions, we have determined the fragmentation of DNA in C6 ($2 \times 10^3$) cell cultures at 4, 16, 24 and 48 hours. The control cultures did not receive any treatment while from 50 to 200 μM (FIG. 3A) of the potassium salt of the 2,5-dihydroxybenzenesulfonic acid were added to the experimental cultures. Experiments were also conducted adding from 25 to 100 μM of the calcium salt of the 2,5-dihydroxybenzenesulfonic acid (FIG. 3B). All experiments were performed in triplicate in three different experiments.

FIGS. 3A and 3B show the following: a) the antiproliferative effect of the 2,5-dihydroxybenzenesulfonic acid is mainly mediated by a proapoptotic activity; b) the cation bonded to the molecule does not determine the activity of the compound because the proapoptotic effect is similar using the calcium or potassium salt of the compound; c) the highest proapoptotic effect is obtained in cells treated with the compound during 48 hours; d) the maximum effect is obtained with a concentration of 25 μM for the calcium salt and 50 μM for the potassium salt, identical to the $IC_{50}$ in cellular proliferation studies. Once it is proven that the antiproliferative mechanism of the 2,5-dihydroxybenzenesulfonic acid participates in the cell death due to apoptosis, we quantitatively evaluated such effect through a microscopic study of gliomic cells using the following technique:
In Situ Detection of Apoptotic Nuclei (TUNEL Technique)

Three independent experiments were made, repeated three times. The C6 cells from control cultures and those from cultures treated during 24 hours with the (50 μM and 100 μM of the calcium and potassium salts respectively) were adhered to glass slides and fixed with a 4% paraformaldehyde buffered solution (pH 7.4) for one hour at the laboratory temperature. Afterwards, the cells were washed and permeabilized with a 0.1% solution of Triton X-100. Then the cells were washed before applying the TUNEL technique [(terminal deoxynucleotidyl transferase (TdT)-mediated dUTP nick and labeling (Gavrieli Y, Sherman Y, Bensasson S A. J Cell Biol 119: 493-501, 1992). A kit for in situ detection of apoptotic nuclei (In situ Cell Death Detection Kit Boehringer Mannheim, Mannheim, Germany) was used. The different stages of the technique were followed in accordance with the instructions of the kit manufacturer. Finally, the cells were colored with green light (Fluka, AG, Switzerland). The TUNEL reaction only appears in the apoptotic nuclei.

Although very similar results were obtained with the calcium and potassium salt of the compound object of the invention, only the results obtained with the potassium salt of the compound are shown. Cells were counted in 6 different fields in twelve slides where the cells from the 6 control cultures and the 6 cultures treated with the 2,5-dihydroxybenzenesulfonic acid (100 μM) had adhered. The total number of non apoptotic and apoptotic cells was as follows:

| C6 Cells | Apoptotic Nuclei | Normal Nuclei |
|---|---|---|
| Control Cells | 138 | 5954 |
| Treated Cells | 3846 | 354 |

The total number of treated cells is lower than the total number of control cells due to the antiproliferative effect of the compound.

Figure 4:

The images of FIG. 4 show an area of an experiment of a control culture (A and B) and of another culture treated with the compound (C and D) in which the TUNEL technique was employed. As shown in the images, only two apoptotic nuclei are observed on the control cells while in the treated cells with the compound object of the invention there are 107 apoptotic nuclei and only 8 normal nuclei (non apoptotic).

These data show that the 2,5-dihydroxybenzenesulfonic acid is a compound with an important proapoptotic activity useful to induce tumor apoptosis. Given that it has been proven that the 2,5-dihydroxybenzenesulfonic acid inhibits apoptosis in normal human cells (Braber R, Farine J C, Lora G A. Apoptosis 4: 4111-49, 1998), this compound is a strong molecule candidate for treatment of cancer.

One of the mechanisms involved in the therapeutic failure of chemotherapy and radiotherapy is the inefficacy of these treatments to induce cellular death by apoptosis, mainly due to the hyper expression of antiapoptotic proteins in tumor cells (Sellers W R, Fisher D E. J Clin Invest 104: 1655-1661, 1999; Branch P. et al. Oncogene 19: 3138-3145, 2000). Therefore, the proapoptotic compounds may be of great clinical use as an adjuvant in chemotherapy and radiotherapy treatments.

Once the proapoptotic effect of the 2,5-dihydroxybenzenesulfonic acid was demonstrated, we evaluated the ability of this compound to increase the antiproliferative effect of the different cytostatic medicines. The following example demonstrates how the 2,5-dihydroxybenzenesulfonic acid is capable of increasing the therapeutic efficacy of the different cytostatic compounds used in oncology such as cisplatin, vincristine, paclitaxel and 5-fluorouracil.

Example 3

Illustrative Assay of the Ability of the 2,5-Dihydroxybenzene Sulfonic Acid in Potentiation of Chemotherapy We used for this study C6 cells cultured in vitro under the same conditions described in example $1.1 \times 10^3$ cells per well were cultured in 24-well plates. Three types of treatment were made: a) 24 hours after the seeding, the cells were separately treated with each one of the following medicines; cisplatin (5 µg/ml), vincristine (0.1 µg/ml), paclitaxel (5 µg/ml) and 5-fluorouracil (100 µg/ml); b) 24 hours after the seeding, the cells were treated jointly with the 2,5-dihydroxybenzenesulfonic acid (potassium salt, 100 µM) and with each one of the following medicines; cisplatin (5 µg/ml) vincristine (0.1 µg/ml), paclitaxel (5 µg/ml) and 5-fluorouracil (100 µg/ml); c) at the time of the seeding (Day 0), the cells were pre-treated with the 2,5-dihydroxybenzenesulfonic acid (potassium salt, 100 µM). Next day the cultures were treated also with each one of the following medicines: cisplatin (5 µg/ml) vincristine (0.1 µg/ml), paclitaxel (5 µg/ml) and 5-fluorouracil (100 µg/ml). The control cultures did not receive treatment for 2 days. After 48 hours (day 2), the cells of identical shape to the ones used in example 1 were evaluated in all the cultures. This study was carried out in triplicate independent experiments repeated three times.

Figure 5:
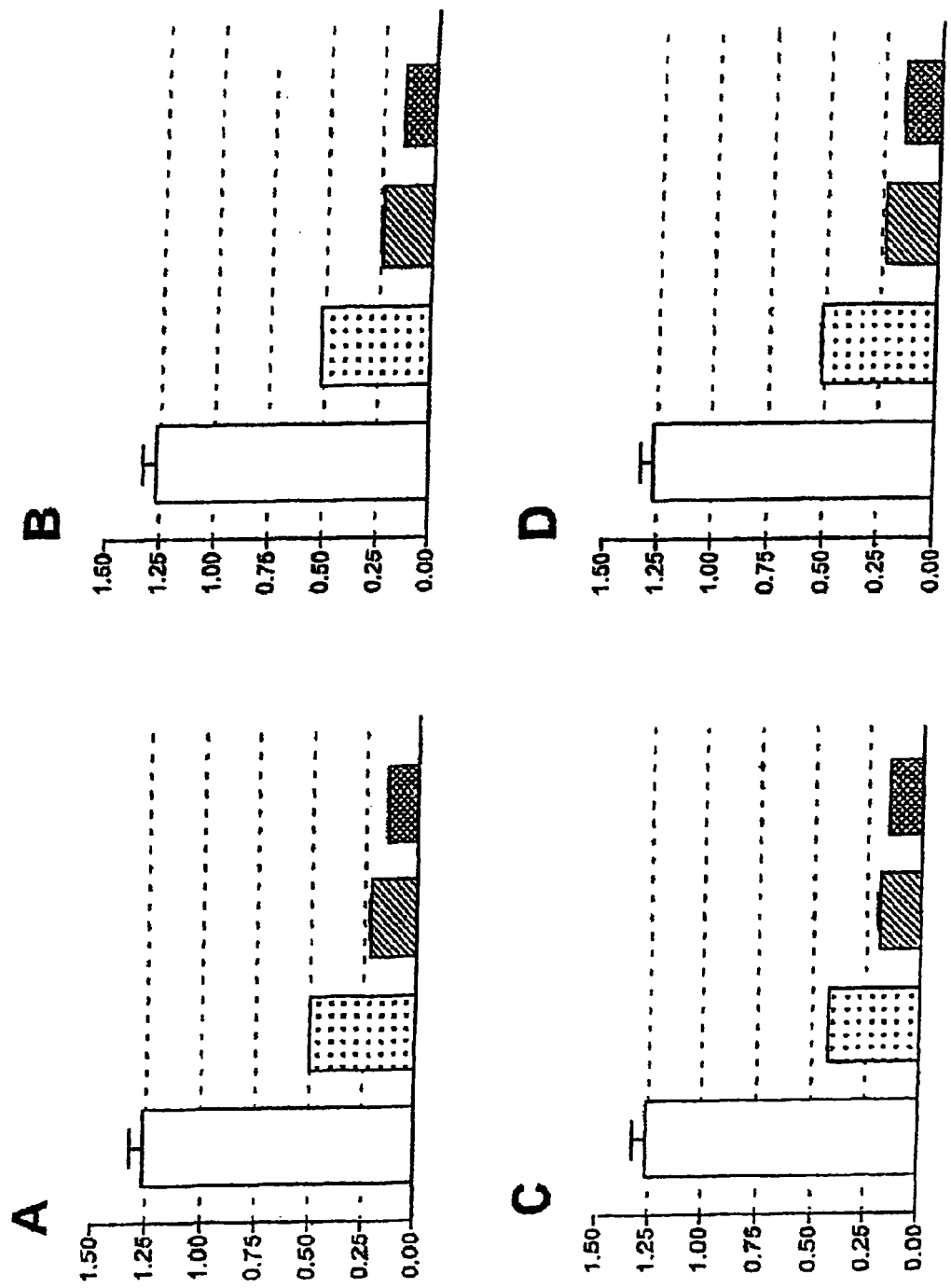

FIG. 5(A, B, C and D) shows the histograms of the experiments performed to evaluate the effect of the 2,5-dihydroxybenzenesulfonic acid in the potentiation of the different cytostatic medicines. Treatment with cisplatin, vincristine and 5-fluorouracil produces an inhibition of 50% in proliferation of C6 cells, while the treatment with paclitaxel obtains 67% of inhibition of the cellular proliferation. The combined treatment of the 2,5-dihydroxybenzenesulfonic acid+the cytostatic medicines (cysplatin, vincristine and 5-fluorouracil) produces an inhibition of 84% in cellular proliferation. The combined treatment with 2,5-dihydroxybenzenesulfonic acid+paclitaxel produces 86% in the inhibition of the cellular proliferation. When cellular cultures are pre-treated with the 2,5-dihydroxybenzenesulfonic acid and afterwards with the following cytostatic medicines: cisplatin, vincristine and 5-fluorouracil, an inhibition of 90% is obtained in the cell proliferation. When paclitaxel is used, the inhibition in cellular proliferation reaches up to 92%.

The above mentioned results demonstrate that the simultaneous treatment of the 2,5-dihydroxybenzenesulfonic acid with the chemotherapeutical agents, increases their therapeutic efficacy and besides this chemical potentiation effect is higher when the cells has been pre-treated with the 2,5-dihydroxybenzenesulfonic acid. These data support the use of the 2,5-dihydroxybenzenesulfonic acid as an adjuvant in the treatment associated with chemotherapy and radiotherapy.

Example 4

Figure 6:
Figure 7:
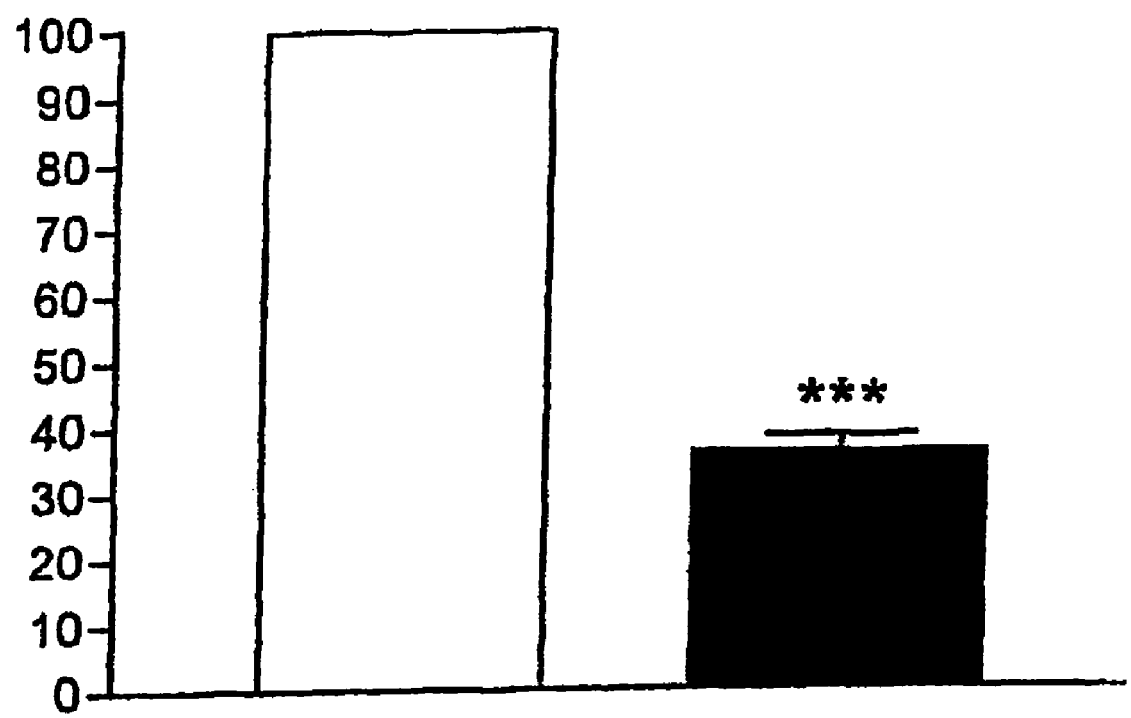

Illustrative Assay of the Antimigration Ability of the 2,5Dihydroxybenzenesulfonic Acid This assay was carried out in three different triplicate experiments. To evaluate the ability of the 2,5-dihydroxybenzenesulfonic acid in the inhibition of cellular migration C6 $2\times10^5$ cells cultured in vitro in 20 mm plates were used. A longitudinal lesion was made with a sterile micropipette (day 0) to the control cultures and in cultures treated with 100 µM of the potassium salt of the 2,5-dihydroxybenzenesulfonic acid. Digital photos were taken using a photographic system connected to a luminous microscope and the area of the lesion was delimited using a computerized morphometric program (Moticam. Motic. Barcelona). Photographs were taken again after 24 hours, and the borders of the lesion were marked overlapping the first two photos (day 0) with those obtained after 24 hours to calculate the percentage of the injured area covered by the migratory cells. These values were represented as a percentage of the regeneration obtained with the treatment. FIG. 6 shows a typical example of a control experiment (A) and another experiment in which the cells were treated during 24 hours with the compound object of the invention (B). As observed in this Figure, the non treated cells completely regenerate the lesion (FIG. 6A) while the cells treated with the compound are not capable of migrating and cover all the area of the lesion (FIG. 6B). FIG. 7 that represents the percentage data of all the experiments shows that the 2,5-dihydroxybenzenesulfonic acid inhibits up to 64% of migration of tumor cells.

Example 5

Illustrative Assay of the Antiangiogenic Ability of the 2,5-Dihydroxybenzenesulfonic Acid We used for this assay the chorioallantoic membrane of a chick embryo for testing the activity of antiangiogenic substances in vivo (Zilberberg L. et al. J Biol Chem 2003; 278: 35564-35573). We used a proangiogenic compound, the basic form of the fibroblast growth factor (bFGF) (Meghna U et al. Blood 2003; 102: 2108-2114).

Fertilized eggs are kept in a incubator at 37° C. with a humidity of 80%. After 4 days, a hole is made in the narrowest end of the egg shell to collect 1 ml of albumin. Then, the hole is covered with a paraffin film (Parafilm M Laboratory Film Chicago Ill. USA). This procedure allows creating an air chamber that prevents the embryo to adhere to the upper part of the shell. On day 13 of incubation, the shell is split at the air chamber level to perform the treatment. Twenty embryos are treated with 5 µl of a solution of 3 µg of bFGF+0.1% heparin, soaked in a nitrocellulose paper disc. Afterwards the shell is sealed with a paraffin film. Next day, in half of the embryos (n=10) the shell is uncovered to soak again the nitrocellulose paper disc with 100 µM of potassium salt of the 2,5-dihydroxybenzenesulfonic acid dissolved in physiological saline (5 µl). The hole in the shell is then covered again with a paraffin film. On day 17 the experiment ends taking photographs of the nitrocellulose piece for the comparison study.

Figure 8:
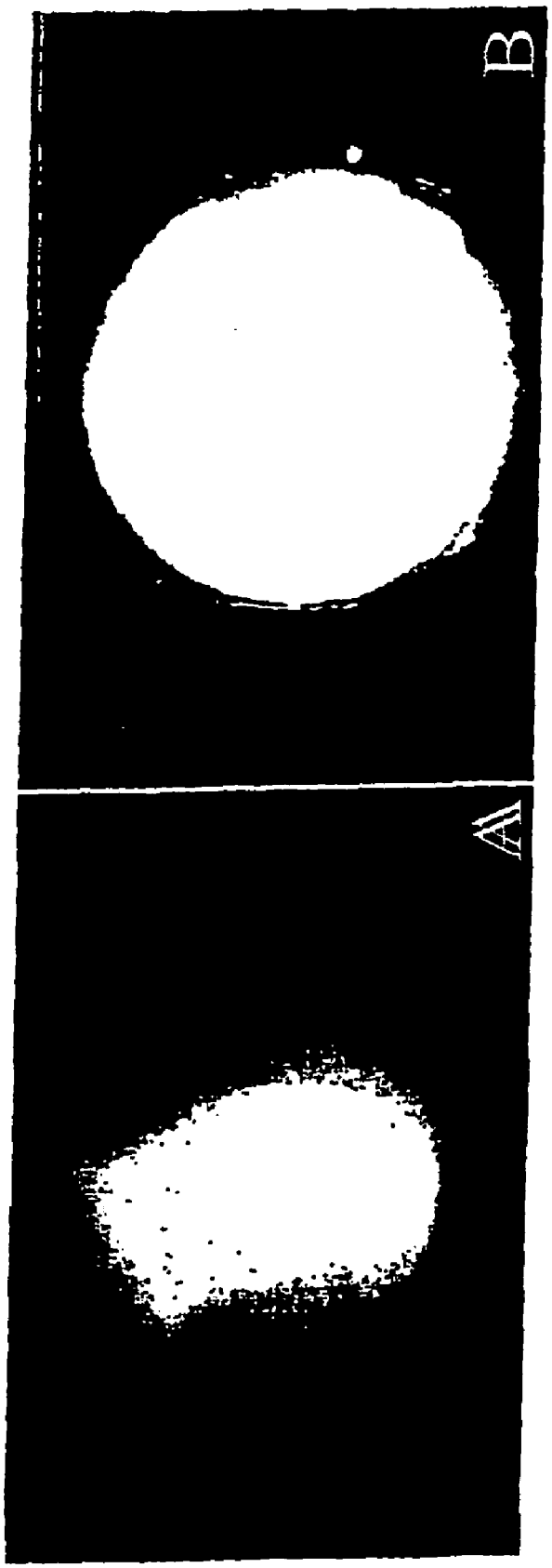

FIG. 8 presents two images corresponding to an embryo treated with 3 µg of bFGF+0, 1% heparin (A) and another embryo to which further, 100 µM of a potassium salt solution of the 2,5-dihydroxybenzenesulfonic acid was added on the next day (B). Image A shows how the nitrocellulose disc is invaded by blood vessels while Image B shows a very scarce vascular invasion in the disc. The morphometric quantification of the images of the nitrocellulose discs using a computerized system (Moticam Motic. Barcelona) shows the antiangiogenic effect of the compound (area of the disc covered by blood vessels in embryos treated with bFGF+heparin=35±8.6% vs. area of the disc covered by blood vessels in embryos treated with bFGF+heparin+potassium salt of the 2,5-dihydroxybenzene sulfonic acid=2±1.5%; $p<0.0001$; unpaired student's t-test). Similar effects were obtained using 50 µM of the calcium salt of the compound. This experiment shows that the compound object of this invention has an antiangiogenic activity for being capable of neutralizing the angiogenic effect induced by bFGF.

Example 6

Assay on Psoriatic Lesions

We used for this study the potassium salt of the 2,5-dihydroxybenzenesulfonic acid formulated at 2.5 and 5% in cream for being this type of formulation a usual procedure for topical treatment of skin diseases. The selected concentrations of the salts of the 2,5-dihydroxybenzenesulfonic acid are within the range of the concentrations used for treatment of diabetic retinopathies: 6 tablets per day of 500 mg of calcium salt of the 2,5-dihydroxybenzenesulfonic acid (Benakis A et al Thérapie 1974; 29: 211-219). As aqueous phase of the cream we have used distilled water. The fatty phase can be constituted by cetylic alcohol, stearic alcohol or vaseline. The span is an efficient emulsifier in the preparation of the cream. Although both formulations (2.5 and 5%) of the product show to be clinically efficient, the best therapeutic benefit is obtained with the concentration at 5%. Therefore, we present the results obtained with the acid formulated in the cream at 5%. The following example illustrates the formulation of an efficient cream for the topic treatment of psoriasis, by way of example and not of limitation of the scope of the invention.

I.—Active Part (potassium salt of the 2,5-dihydroxybenzenesulfonic acid at 5.6%)

II.—Inactive Part (as excipients cetylic alcohol (2.5%), stearyl alcohol (2.5%), liquid vaseline (30%), white soft paraffin (20%), sorbitan oleate (5%) and distilled water (c.s.p. 100 g).

Figure 9:
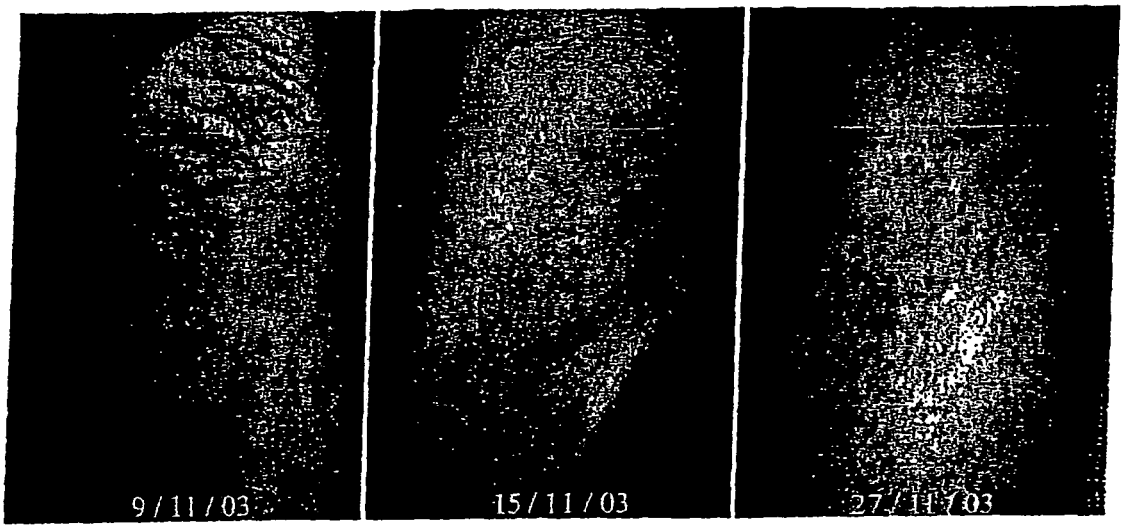

The clinical efficacy of the treatment was evaluated according to the index that quantifies the desquamation signs (D), erythema (E) and infiltration (I) to which the following assessment was assigned: (0) absent; (1) slight; (2) moderate and (3) severe (Freeman A K et al. J. Am. Acad Dermat 2003; 48: 564-568). FIG. 9 shows three images: before treatment, six and thirteen days after treatment of the same chronic psoriatic plaque located in the extension area of the left elbow treated with the potassium salt of the 2,5-dihydroxybenzenesulfonic acid at 5%. As can be observed, the topical treatment two times at day with a cream containing the potassium salt of the 2,5-dihydroxybenzene sulfonic acid produces an early (6 days) very notable "clearance" of the plaque with almost total disappearance of hyperkeratosis. The therapeutic efficacy of the cream is more evident at the end of the second week of treatment. The treatment produces a significant reduction of the global values of the DEI index (DEI global pre-treatment=6±1.57 vs. DEI global post-treatment=1±0.58; $p<0.0001$; unpaired student's t-test).

Figures Captions

1. Histogram showing the antiproliferative effect of the treatment with different concentrations of the (A) calcium and (B) potassium salts of the 2,5-dihydroxybenzenesulfonic acid in cultures of C6 cells after 48 hours of treatment. Ordinates: Absorbance at 595 nm; Abscises: concentration: μM.
2. Panel A shows the aspect of a control culture of C6 cells after 48 hours. Panel B shows an image of a culture of C6 cells treated during 48 hours with 50 μM of the 2,5-dihydroxybenzenesulfonic acid (calcium salt). Panel C shows a culture of C6 treated during 48 hours with 100 μM of the potassium salt of the 2,5-dihydroxybenzenesulfonic acid.
3. Representative histograms in which it is observed that the antiproliferative effect of the 2,5-dihydroxybenzenesulfonic acid is not due to necrosis (white histogram) but to apoptosis (lined histogram). A: treatment with the calcium salt of the 2,5-dihydroxybenzenesulfonic acid. B: Treatment with the potassium salt of the 2,5-dihydroxybenzenesulfonic acid. Ordinates: Absorbance at 405 nm; Abscises: time in hours.
4. Images of gliomic C6 cells processed with the TUNEL technique for in-situ detection of apoptotic cells. The apoptotic nuclei are shown dark and the nucleus and cytoplasm of the cell of the non apoptotic cells are shown in light color. The arrows indicate apoptotic nucleus. A and B control cells, C and D cells treated with 2,5-dihydroxybenzenesulfonic acid. Photographs B and D correspond to a zoom of the boxes of A and C photographs respectively.
5. Histograms demonstrating the potentiating effect on chemotherapy (assessed as an antiproliferative effect) of the 2,5-dihydroxybenzenesulfonic acid, with different cytostatic compounds A) Cisplatin (5 μg/ml); B) Vincristine (0.1 μl/ml); C) Paclitaxel (5 Ug/ml) and D) 5-fluorourasil (100 μg/ml). Ordinates: Absorbance 595 nm; Abscises: white histogram (control); dotted (cytostatic; day 1); lined histogram (2,5-dihydroxybenzenesulfonic acid+cytostatic; day 1); squared histogram (2,5-dihydroxybenzenesulfonic acid (day 0)+cytostatic; day 1).
6. Photographic images of cellular migration in a control experiment and other experiments where the cells were treated with the 2,5-dihydroxybenzenesulfonic acid (B). The control cells totally regenerate one lesion made during the culture, while the cellular migration of the cells treated with the 2,5-dihydroxybenzenesulfonic acid, was unable to fully cover the affected area of the culture. The horizontal lines delimit the initial longitudinal lesion made in the cultures.
7. Histogram representing the migratory ability of the C6 cells in controlled cultures (white histogram) and in cultures treated with the 2,5-dihydroxybenzenesulfonic acid (black histogram). The migratory ability is expressed (ordinates) as a percentage of regeneration (percentage of the area covered of a longitudinal lesion made in the cultures)
8. Images of two chicken embryos with 17 days of incubation. Panel A corresponds to an embryo treated with 3 μg of bFGF+0.1% of heparin. Panel B shows the aspect of an embryo treated with 3 μg of bFGF+0.1% de heparin+ 100 μM of the potassium salt of the 2,5-dihydroxybenzenesulfonic acid. Panel A shows the antiangiogenic effect of the 2,5-dihydroxybenzenesulfonic acid because the nitrocellulose disc used as releasing vehicle of the substance appears almost totally devoid of vessels.
9. Images of a hiperkeratosic psoriatic plaque located in the rear region of the left elbow. Image A represents the aspect of the psoriatic plaque before initiating treatment. Image B is an aspect of the same plaque after six days of treatment with a cream at 5% containing as an active component the potassium salt of the 2,5-dihydroxybenzenesulfonic acid. Image C shows the aspect of the psoriatic plaque after two weeks of treatment with the potassium salt of the 2,5-dihydroxybenzenesulfonic acid formulated at 5%. The numbers shown in the images correspond to the day on which the photographs were taken.

The invention claimed is:

1. A method of treating an angiodependent disease, wherein the angiodependent disease is psoriasis, comprising topically administering 2,5-dihydroxybenzenesulfonic acid or of any of its pharmaceutically acceptable salts to an individual in need thereof.

2. The method of claim 1, wherein the pharmaceutically acceptable salt is the potassium salt of the 2,5-dihydroxybenzene sulfonic acid.

3. The method of claim 1, wherein the pharmaceutically acceptable salt is the calcium salt of the 2,5-dihydroxybenzene sulfonic acid.

4. The method of claim 1, wherein the 2,5-dihydroxybenzenesulfonic acid compound is formulated with at least one pharmaceutically acceptable excipient.

5. The method of claim 1, wherein the 2,5-dihydroxybenzenesulfonic acid compound is formulated as a cream or unguent whose composition includes:
- A pharmaceutically efficient amount of the 2,5-dihydroxybenzenesulfonic acid or of any of its pharmaceutically acceptable salts;
- A pharmaceutically acceptable amount of at least one alcohol;
- A pharmaceutically acceptable amount of at least one emulsifier;
- A pharmaceutically acceptable amount of at least one excipient;
- A pharmaceutically acceptable amount of at least one excipient comprising a lipid phase; and
- Distilled water.

6. The method of claim 5, wherein the cream or unguent comprises:
- 5% of the potassium salt of the 2,5-dihydroxybenzenesulfonic acid;
- 2.5% of cetylic alcohol;
- 2.5% of stearic alcohol;
- 30% of liquid Vaseline;
- 30% of white soft paraffin;
- 5% span (sorbitan oleate); and
- q.s 100 g of distilled water.

* * * * *